United States Patent [19]

Weinberger

[11] Patent Number: Plant 5,487

[45] Date of Patent: Jun. 4, 1985

[54] PLUM TREE, SUPLUMFIFTEEN

[75] Inventor: John H. Weinberger, Fresno, Calif.

[73] Assignee: Superior Farming Company, Bakersfield, Calif.

[21] Appl. No.: 555,191

[22] Filed: Nov. 25, 1983

[51] Int. Cl.[3] ..... A01H 5/00

[52] U.S. Cl. ..... Plt./38

[58] Field of Search ..... Plt./38

*Primary Examiner*—James R. Feyrer

*Attorney, Agent, or Firm*—Huebner & Worrel

[57] ABSTRACT

A plum tree generally similar to the Simka Plum Tree (U.S. Plant Pat. No. 1,882) which it most nearly resembles, bearing large, dark purple fruit, but which ripens about three weeks later than that of Simka, is larger, and is clingstone.

1 Drawing Figure

BACKGROUND OF THE NEW VARIETY

The present invention relates to a new and distinct variety of plum tree broadly characterized by its very productive and regular bearing of fruit which is uniformly large and globose in shape, and having a dark purple skin which is tenacious to pale yellow flesh, the flesh clinging over the entire surface of the stone. The new variety further is broadly characterized by its general similarly to the Simka Plum Tree (U.S. Plant Pat. No. 1,882), differing therefrom in several important characteristics including the greater size of its fruit and the ripening thereof about three weeks later than that of the Simka.

It has long been recognized that prospective consumers of fruit, and in particular potential purchasers of plums, are influenced in their buying decisions, in large part, by the aesthetic appeal of a given variety. The Simka Plum Tree has long been known as a regular bearer of large, rose ebony colored fruit having pale yellow flesh. However, while the Simka has obtained a certain degree of commercial success, it has long been known that it would be desirable to provide a plum broadly similar thereto but which ripens later than the Simka in order to provide a dark-skinned, attractive fruit at a time during the season when few varieties of similarly appearing plums are available. Further, it has long been known that it would be desirable to provide such a plum having not only an attractive, even exterior coloration but also having an aesthetically pleasing, uniformly globose form with firm, delicately-flavored flesh.

ORIGIN AND ASEXUAL REPRODUCTION OF THE NEW VARIETY

The new variety of plum tree was discovered by me in 1980 growing as a seedling in an orchard located at 5090 East Church Avenue in Fresno, Calif., and owned by the Superior Farming Company of Bakersfield, Calif. The seedling resulted from a planned breeding program conducted and supervised by me at the aforementioned location on behalf of Superior Farming Company, and the seed resulted from an open pollination of a flower of a Simka Plum Tree.

I asexually reproduced the new variety in 1980 by budding the variety into other trees or rootstocks located at the above-identified address, and the fruit and tree characteristics resulting from such budding proved identical to those of the original hybrid seedling.

SUMMARY OF THE NEW VARIETY

The instant variety of plum tree is characterized by its general similarity to the Simka Plum Tree (U.S. Plant Pat. No. 1,882), but has the important distinction of ripening approximately three weeks later. Further, the fruit is larger than that of Simka and is cling rather than freestone.

The new variety is a very productive and regular bearer of large, globose fruit having evenly colored, dark purplish skin. The fruit of the new variety has pale yellow, firm-textured flesh which ripens evenly with abundant rich juice and a delicate, superior eating flavor. The flesh clings to the stone over the entire surface thereof.

BRIEF DESCRIPTION OF THE DRAWING

The accompanying drawing is a color photograph of three mature plums of the subject variety with one plum divided to show the flesh color and stone characteristics, together with a stone which has been removed from another mature plum and a representative twig showing characteristic leaves.

DETAILED DESCRIPTION

Referring more specifically to the pomological details of this new and distinct variety of plum tree, the following has been observed under the ecological conditions prevailing in the designated orchard in Fresno County, Calif. All of the color code plate indications are by reference to the Munsell Limit Color Cascade, except where common terms of color definition are employed.

TREE

Size: Medium to small.
Vigor: Medium.
Figure: Upright, vase-formed.
Productivity: Very productive.
Regularity of bearing: Regular.
Trunk:
- *Thickness.*—Medium.
- *Texture of bark.*—Medium.

Branches:
- *Thickness.*—Medium.
- *Texture.*—Medium.
- *Color.*—Brown on older wood; glossy green on new shoots.

*Lenticels.*—Medium in number; small in size.

Leaves:

*Size.*—Medium; length — 12.0 cm.; width — 4.6 cm.

*Form.*—Oval, accuminate; abruptly pointed.

*Thickness.*—Medium.

*Color.*—Medium green.

*Texture.*—Smooth.

*Marginal form.*—Crenate.

*Petiole.*—Length — medium; thickness — medium.

*Glands.*—Average number 2, irregular; opposite; small; globose; green; positioned at base of blade, on petiole.

*Stipules.*—Present.

Flower buds: Small, short, plump, free.

Flowers: Small, white; date of full bloom — Feb. 28 in 1983, medium compared with other varieties.

FRUIT

Maturity:

*Date of first pick.*—Aug. 10, 1983.

*Date of last pick.*—Aug. 20, 1983.

Size: Uniform, large; axial diameter — 6.2 cm; diameter transverse in suture plane — 6.6 cm.; diameter at right angles to suture plane — 6.6 cm.

Form: Uniform, globose.

*Suture.*—Inconspicuous shallow line extending from base to apex.

*Ventral surface.*—Rounded throughout; lips equal.

*Cavity.*—Rounded, circular; depth — 7 mm.; breadth — 24 mm.

*Base.*—Rounded.

*Apex.*—Rounded.

*Pistil point.*—Apical.

*Stem.*—Length — medium; caliper — medium.

Skin: Medium thickness; medium texture; tenacious to flesh; slight tendency to crack.

*Color.*—Plate 2-15.

*Down.*—Wanting.

Flesh:

*Color.*—Pale Yellow, Plate 26-3; surface of pit cavity — Pale Yellow, Plate 28-11.

*Amygdalin.*—Wanting.

*Juice.*—Abundant, rich.

*Texture.*—Firm, fine.

*Fibers.*—Few, fine, tender.

*Ripening.*—Even.

*Flavor.*—Delicate.

*Aroma.*—Wanting.

*Eating quality.*—Excellent.

Stone: Cling; adheres to flesh over entire surface; short fibers.

*Size.*—Medium; length — 2.3 cm.; breadth — 2.0 cm.; thickness — 1.2 cm.

*Form.*—Globose.

*Base.*—Straight.

*Hilum.*—Narrow oval.

*Apex.*—Rounded.

*Sides.*—Equal.

*Ridges.*—Rounded toward base.

*Ventral edge.*—Thin, with wing throughout.

*Dorsal edge.*—Narrow with shallow narrow groove.

*Color.*—Plate 28-11.

*Tendency to split.*—Slight in dry season.

Use: Fresh market; dessert.

Keeping quality: Good.

Shipping quality: Good.

Although the new variety of plum tree possesses the described characteristics as a result of the growing conditions in Fresno County, Calif., in the central part of the San Joaquin Valley, it is to be understood that variations of the usual magnitude in characteristics incident to growing conditions, fertilization, pruning and pest control are to be expected.

Having thus described and illustrated my new variety of plum tree, what I claim as new and desire to secure by Letters Patent is:

1. A new and distinct variety of plum tree substantially as illustrated and described, characterized particularly as to novelty by its general similarity to the Simka Plum Tree (U.S. Plant Pat. No. 1,882) in its regular and productive bearing of large, dark purplish skinned fruit having firm, pale yellow flesh, but differing therefrom in the greater size of its fruit, the ripening of its fruit about three weeks later than that of the Simka, and its flesh which clings over the entire surface of the stone.

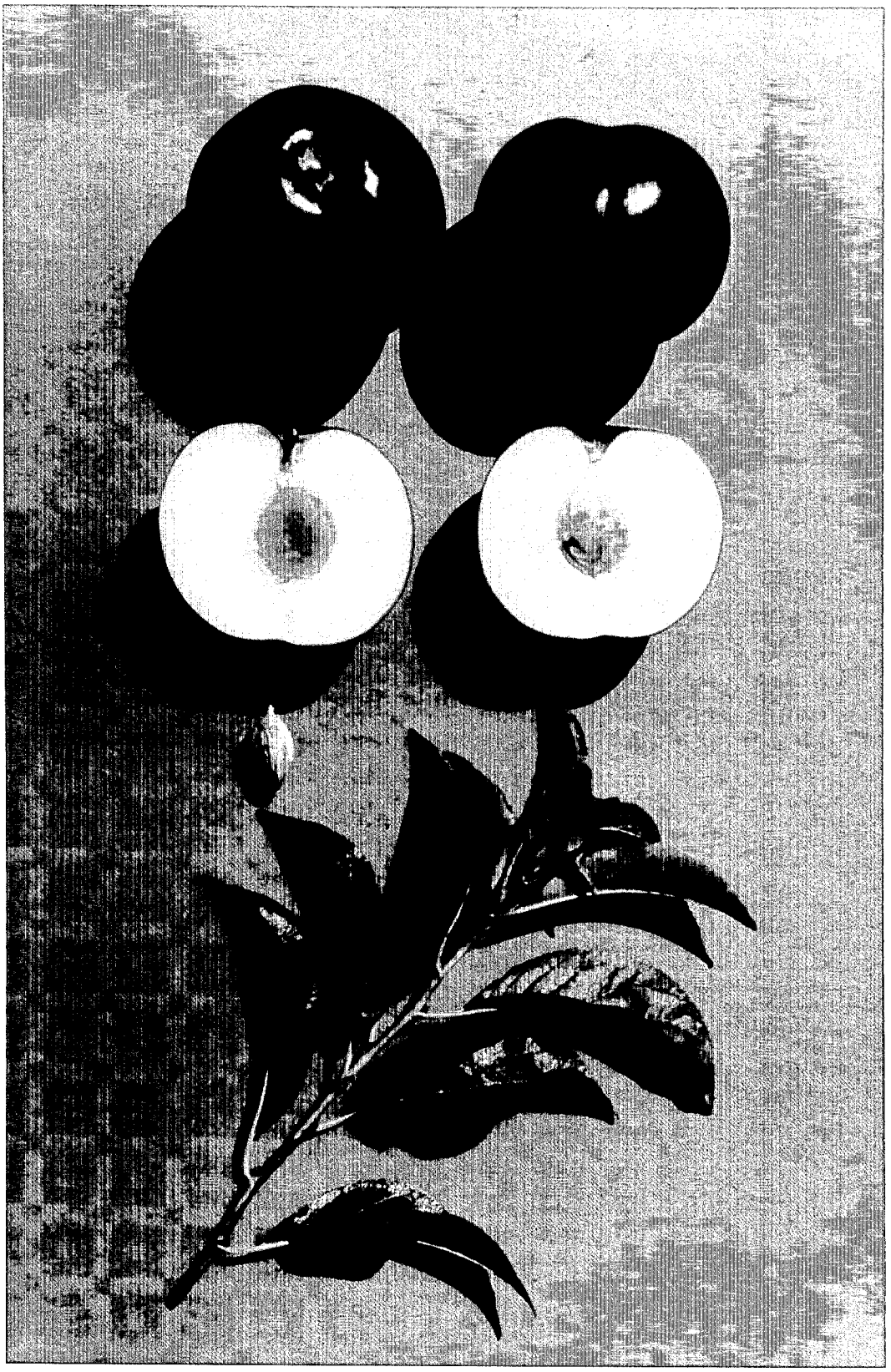

* * * * *